(12) United States Patent
Webb et al.

(10) Patent No.: US 7,754,241 B1
(45) Date of Patent: Jul. 13, 2010

(54) MACROMONOMER FOR PREPARATION OF A DEGRADABLE HYDROGEL

(75) Inventors: Charles K. Webb, Clemson, SC (US); Naren R. Vyavahare, Easley, SC (US)

(73) Assignee: Clemson University Research Foundation

( * ) Notice: Subject to any disclaimer, the term of this patent is extended or adjusted under 35 U.S.C. 154(b) by 478 days.

(21) Appl. No.: 11/271,405

(22) Filed: Nov. 10, 2005

Related U.S. Application Data

(60) Provisional application No. 60/627,505, filed on Nov. 12, 2004.

(51) Int. Cl.
| | |
|---|---|
| A61K 9/14 | (2006.01) |
| A61K 9/00 | (2006.01) |
| C12N 11/08 | (2006.01) |
| C12N 11/04 | (2006.01) |
| C07K 17/04 | (2006.01) |
| C07K 17/08 | (2006.01) |

(52) U.S. Cl. ............... 424/486; 424/400; 424/423; 424/487; 435/180; 435/182; 530/815; 530/817

(58) Field of Classification Search ............ None
See application file for complete search history.

(56) References Cited

U.S. PATENT DOCUMENTS

| | | | |
|---|---|---|---|
| 3,918,455 A | 11/1975 | Coplan | 128/339 |
| 3,997,396 A | 12/1976 | Delente | 195/1.8 |
| 5,162,225 A | 11/1992 | Sager et al. | 435/240.243 |
| 5,200,248 A | 4/1993 | Thompson et al. | 428/131 |
| 5,242,644 A | 9/1993 | Thompson et al. | 264/177.15 |
| 5,263,984 A | 11/1993 | Li et al. | 623/15 |
| 5,268,229 A | 12/1993 | Phillips et al. | 428/400 |
| 5,512,600 A | 4/1996 | Mikos et al. | 521/61 |
| 5,518,680 A | 5/1996 | Cima et al. | 264/401 |
| 5,611,981 A | 3/1997 | Phillips et al. | 264/130 |
| 5,716,404 A | 2/1998 | Vacanti et al. | 623/8 |
| 5,723,159 A | 3/1998 | Phillips et al. | 425/461 |
| 5,770,193 A | 6/1998 | Vacanti et al. | 424/93.7 |
| 5,906,828 A | 5/1999 | Cima et al. | 424/423 |
| 5,942,436 A | 8/1999 | Dunn et al. | 435/325 |
| 5,972,505 A | 10/1999 | Phillips et al. | 428/397 |
| 6,303,136 B1 | 10/2001 | Li et al. | 424/424 |
| 6,306,424 B1 | 10/2001 | Vyakarnam et al. | 424/426 |
| 6,333,029 B1 | 12/2001 | Vyakarnam et al. | 424/93.1 |
| 6,368,859 B1 | 4/2002 | Atala | 435/395 |
| 6,521,431 B1 * | 2/2003 | Kiser et al. | 435/177 |
| 7,056,580 B2 | 6/2006 | Dugan | 428/372 |
| 2001/0033857 A1 | 10/2001 | Vyakarnam et al. | 424/443 |
| 2002/0022883 A1 | 2/2002 | Burg | 623/8 |
| 2005/0070930 A1 | 3/2005 | Kammerer | 606/151 |

OTHER PUBLICATIONS

U.S. Appl. No. 11/170,890, filed Jun. 30, 2005.
U.S. Appl. No. 11/171,565, filed Jun. 30, 2005.
U.S. Appl. No. 11/605,856, filed Nov. 29, 2006.
U.S. Appl. No. 11/605,870, filed Nov. 29, 2006.
U.S. Appl. No. 11/605,873, filed Nov. 29, 2006.
"Bioerodible Hydrogels Based on Photopolymerized Poly (ethylene glycol)-co-poly(a-hydroxy acid) Diacrylate Macromers," by A. S. Sawhney, C.P. Pathak, and J.A. Hubbell; *Macromolecules 1993*, 26, American Chemical Society, pp. 581-587.
"Characterization of Permeability and Network Structure of Interfacially Photopolymerized Poly (ethylene glycol) Diacrylate Hydrogels," by G.M. Cruise, D.S. Scharp, and J.A. Hubbel, *Biomaterials 19* (1998), Elsevier Science Ltd , pp. 1287-1294.
"Bridging Areas of Injury in the Spinal Cord," by Mary Bartlett Bunge, The Neuroscientist, vol. 7, No. 4, 2001, Sage Publications, pp. 325-339.

* cited by examiner

*Primary Examiner*—David M Naff
(74) *Attorney, Agent, or Firm*—Dority & Manning, P.A.

(57) ABSTRACT

A degradable hydrogel and a method of making a degradable hydrogel is disclosed herein. The method comprises obtaining a hydrophilic polymer having at least two hydroxyl groups, reacting the hydrophilic polymer with a di-functional monomer comprised of an acid halide group and an alkyl halide group to form an intermediate having an ester bond and a terminal alkyl halide group, reacting the terminal alkyl halide group of the intermediate with a metallic salt of a vinyl acid monomer to form a macromonomer comprised of an ester, an alkyl group spacer, and a terminal vinyl group, and polymerizing the macromonomer to form a degradable hydrogel. A method is also disclosed for varying the degradation rate of the hydrogel as a function of the chemical composition of the alkyl group spacer in the terminal linkage of the macromonomer.

15 Claims, 5 Drawing Sheets

US 7,754,241 B1

MACROMONOMER FOR PREPARATION OF A DEGRADABLE HYDROGEL

CROSS-REFERENCE TO RELATED APPLICATIONS

This application is entitled to the benefit of, and claims priority to, provisional U.S. Patent Application Ser. No. 60/627,505, filed on Nov. 12, 2004, which is incorporated herein by reference in its entirety.

FEDERALLY SPONSORED RESEARCH AND DEVELOPMENT

The United States Government may have rights in this invention pursuant to National Science Foundation EpSCOR award EPF-0132573.

BACKGROUND OF THE INVENTION

In an attempt to develop degradable materials such as may be used in biological applications, polymeric matrices have been widely investigated. Degradable matrices have shown potential for many varied uses such as drug delivery agents, scaffolding for tissue growth and development applications, and as in vivo adhesive/barrier agents. High water content materials such as hydrogels formed from cross-linked hydrophilic polymers have been found particularly attractive for both in vivo and ex vivo biological applications. The creation of degradable synthetic hydrogels is particularly desirable for many applications. The use of synthetic materials provides superior control and reproducibility of physical and chemical properties relative to naturally-derived biological polymers, while degradability provides a mechanism for ultimate removal of the material from the body following implantation.

There are numerous methods for hydrogel crosslinking. The creation of degradable synthetic hydrogels has been primarily based on a method developed by Sawheney et al. In this method, hydrophilic polymers containing hydroxyl end groups are used for the ring-opening polymerization of cyclic monomers of alpha hydroxy acids such as glycolide, lactide, and epsilon-caprolactone, resulting in the addition of varying numbers of terminal ester bonds as a function of the degree of polymerization. This method regenerates terminal hydroxyl groups which are subsequently reacted with acryloyl or methacryloyl chloride to generate terminal vinyl groups suitable for free-radical polymerization. While this general method has been widely employed, it is disadvantageous because it requires the use of specialized cyclic monomers that are costly and difficult to obtain in industrial scale quantities, as well as relies upon the use of polymerization reactions which have inherent limitations in controlling the degree of polymerization and reproducibility.

Thus, there is a need for an improved method of making a synthetic degradable hydrogel, particularly a method that may be carried out utilizing common industrial chemical intermediates and alternative reaction schemes. Moreover, there is a need for a synthetic degradable hydrogel that can be readily formed having a controlled, predetermined and consistent degradation rate.

SUMMARY OF THE INVENTION

The present invention is directed to a method for making a degradable hydrogel. The method comprises obtaining a hydrophilic polymer comprising at least two hydroxyl groups; reacting the hydrophilic polymer with a di-functional monomer comprised of an acid halide group and an alkyl halide group to form an intermediate having an ester bond and a terminal alkyl halide group; reacting the terminal alkyl halide group of the intermediate with a metallic salt of a vinyl acid monomer to form a macromonomer comprised of an ester, an alkyl group spacer, and a terminal vinyl group; and polymerizing the macromonomer to form a degradable hydrogel.

The present invention is also directed to the a method of controlling the degradation rate of a synthetic degradable hydrogel.

Furthermore, the present invention relates to the synthetic degradable hydrogel itself as well as suitable end-use applications for the degradable hydrogel including, but not limited to, biomedical applications.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which.

DETAILED DESCRIPTION OF THE INVENTION

Figure 1:
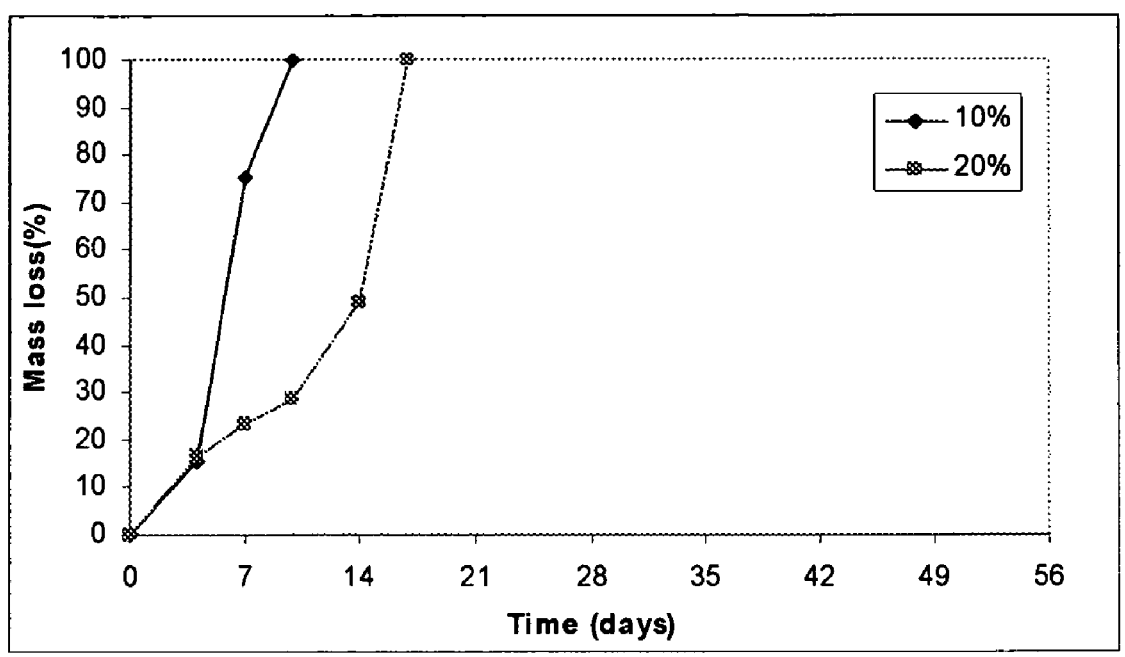
FIG. 1 illustrates the degradation rate of a hydrogel in accordance with the Examples of the present invention.

Reference will now be made in detail to various embodiments of the invention, one or more examples of which are set forth below. Each embodiment is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used in another embodiment to yield a still further embodiment. Thus, it is intended that the present invention cover such modifications and variations as come within the scope of the appended claims and their equivalents.

The term "hydrogel", as used herein, refers to a cross-linked network of hydrophilic polymers.

The term "biologically active agent", as used herein, refers to any material that can exhibit a biological activity including, but not limited to, drugs and therapeutic agents. A biologically active agent may be selected to alter the degradation rate of a hydrogel. Examples of biologically active agents include, but are not limited to, antibiotics, proteins, peptides, oligonucleotides, polysaccharide, vectors, plasmids, small molecules, diagnostic agents including imaging agents, as well as growth and nutrient agents.

The term "small molecule" in reference to a biologically active agent, as used herein, refers to any agent with a molecular weight less than approximately 100,000 Da that can be used to obtain a beneficial effect. Examples include, but are not limited to, small molecule drugs (i.e., low molecular weight therapeutic agents), imaging agents, and other low molecular weight chemical compounds used in medical technologies. The term "small molecule" is intended to encompass any low molecular weight agent that can exhibit a beneficial biological activity including, but not limited to, therapeutic agents.

The present invention is directed to a method for making a synthetic degradable hydrogel. In accordance with the method of the present invention, a hydrophilic polymer is selected as the starting material. The hydrophilic polymer comprises at least two hydroxyl groups. Examples of hydrophilic polymers suitable for use in the present invention include, but are not limited to, polyethylene glycol (PEG), polyvinyl alcohol (PVA), polypropylene glycol, di-and tri-block co-polymers of polyethylene glycol and polypropylene glycol, and any combination thereof. However, polyethylene glycol polymers are preferred. For example, a PEG-based hydrogel may be particularly attractive, for instance, when considering biological applications due to its excellent biocompatibility, its resistance to protein adsorption and cell attachment as well as the biocompatibility of the polymer degradation products.

The hydrophilic polymer may be of any suitable size. For example, the hydrophilic polymer may have a number average molecular weight of about 400 or greater. For example, in some situations it may be desirable for the hydrophilic polymer to have a number average molecular weight between about 400 and about 100,000. However, higher or lower values may also optionally be utilized.

The size of the hydrophilic polymer may be selected to control the cross-linking density of the hydrogel which is a contributing factor in determining the degradation rate of the matrix. In addition, the size of the hydrophilic polymer may be selected to control the mesh size of the product matrix. For example, in those applications in which the hydrogel is intended to encapsulate small molecules, for instance in a drug delivery device, it may be preferred to form a hydrogel with a relatively small mesh size in the matrix. Accordingly, it may be preferred in such situations to utilize hydrophilic polymers of lower molecular weights.

In accordance with the method of the present invention, the hydrophilic polymer is reacted with a di-functional monomer to form an intermediate having an ester bond and a terminal alkyl halide group. The di-functional monomer comprises an acid halide group and an alkyl halide group.

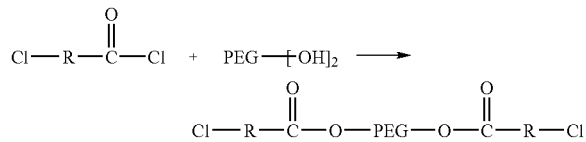

wherein R acts as a spacer and is any straight or branched alkyl group. The alkyl group may be of any length and with or without pendant groups. Preferably, the alkyl group comprises 1 to 10 carbons. Optionally, the alkyl group may be an isoalkyl group. The alkyl group may be selected in order to control the degradation rate of the hydrogel.

In accordance with the method of the present invention, the terminal alkyl halide group of the intermediate is reacted with a metallic salt of a vinyl acid monomer to form a macromonomer as shown below. Alternative metallic salts of acid vinyl monomers incorporating additional alkyl functionality could also be employed. Examples of metallic salts include, but are not limited to, sodium acrylate, sodium methacrylate, potassium methacrylate, and carboxyethyl methacrylate

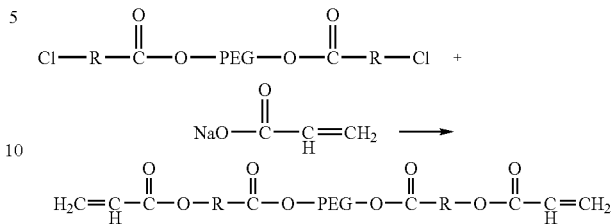

The macromonomer is comprised of a hydrophilic polymer, an ester, an alkyl group spacer R, and a terminal vinyl group. The macromonomer may have a number average molecular weight between about 400 and about 100,000.

In accordance with the method of the present invention, the macromonomer is subsequently polymerized to form the degradable hydrogel. Any polymerization method known to one of ordinary skill in the art may be employed in accordance with the present invention including, but not limited to, redox and photo-initiated free radical polymerization.

A hydrogel prepared in accordance with the present invention may be photopolymerized, for example, in the presence of a suitable photoinitiator such as IRGACURE® or DAROCUR® photoinitiators available from Ciba Specialty Chemicals. Optionally, a cationic initiator may be present. For example, a polyvalent elemental cation such as $Ca^{2+}$, $Mg^{2+}$, $Al^{3+}$, $La^{3+}$, or $Mn^{2+}$ may be used. In another example, a polycationic polypeptide such as polylysine or polyarginine may be utilized as an initiator. Such polymerizations may generally be performed in the presence of biologically active molecules and living cells, as well as either ex vivo or in situ. Polymerization may be performed in the presence of vinyl co-monomers for the introduction of immobilized biologically active agents during polymerization or the introduction of chemically reactive groups for subsequent modification with biologically active agents. Examples of suitable co-monomers include, but are not limited to, acrylate-PEG-peptide conjugates formed from synthetic bioactive peptides and acryloyl-PEG-NHS (Nektar), hydroxyethyl methacrylate and hyodroxyethyl acrylate for introduction of hydroxyl groups, carboxyethyl acrylate for introduction of carboxylic acid groups, aminopropyl methacrylate for incorporation of amine groups, as well as di-functional acrylate/nitrilotriacetic acid moieties for subsequent immobilization of histidine tagged recombinant molecules via metal chelate chemistry.

An advantage of a synthetic degradable hydrogel of the present invention is that it may be formed from readily available, economical starting materials. In addition, the degradable hydrogel of the present invention may be formed with a predetermined, controlled degradation rate. Thus, a degradable hydrogel in accordance with the present invention may be engineered with a specific end-use application in mind. Furthermore, it may be engineered to have a predetermined and controlled life span.

In accordance with the present invention, a hydrogel matrix for use in vivo may be administered to a patient according to a suitable administration method (e.g., orally or percutaneously). In other aspects of the present invention, the systems can be utilized in ex vivo biological applications, for example in tissue engineering applications, or in non-biological applications and as such, the carrier matrix of the invention need not be a self-assembling matrix.

In accordance with the present invention, the hydrogel may be comprised from two or more different macromonomers. Optionally, there may be different macromonomers in discrete locations throughout the hydrogel. For example, the hydrogel may include a hydrolytically degradable portion as described herein, in combination with other portions, for example a second degradable portion formed from a cross-linked ester-alkyl-acrylate terminated macromonomer as herein described, but utilizing a different hydrophilic polymer and/or a different alkyl group on the macromonomer. Optionally, the materials may be combined with other degradable portions and/or may include a non-degradable portion in the hydrogel.

Figure 2:
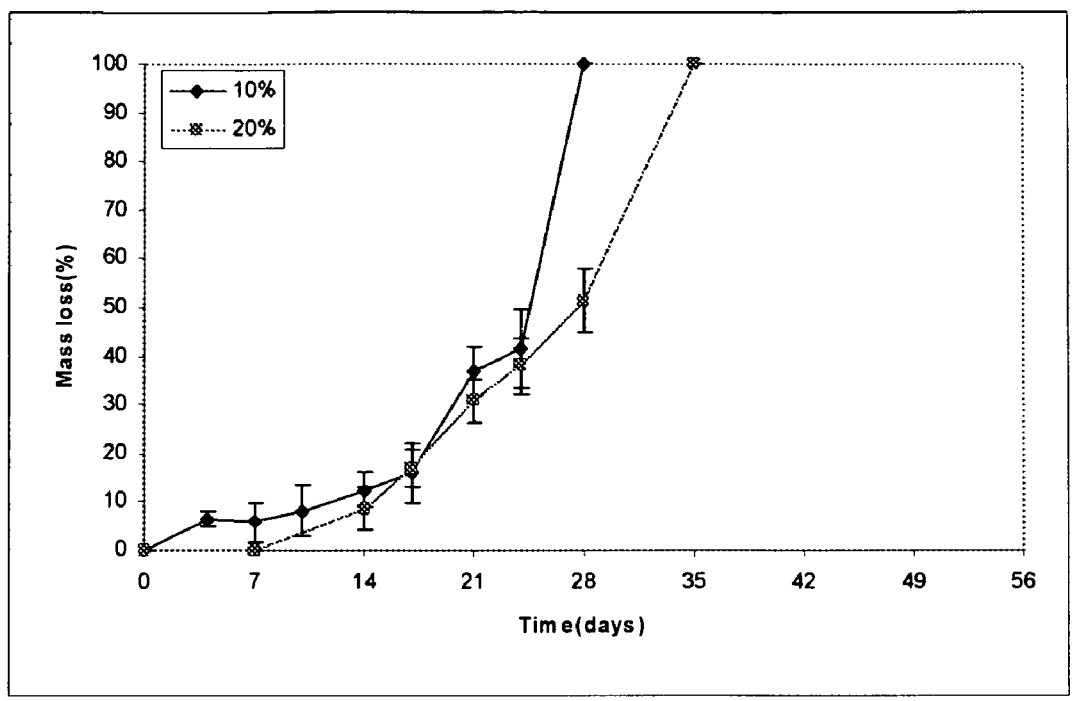
FIG. 2 illustrates the degradation rate of a hydrogel in accordance with the Examples of the present invention.

The degradation rate of the hydrogels has been found to be variable and a function of the chemical composition of the alkyl group in the terminal linkage. Hydrogels containing a single carbon alkyl spacer achieve complete degradation by day 17 versus day 28 for hydrogels cross-linked from macromonomers containing a single carbon alkyl spacer that includes a pendant carbon (FIGS. 1 and 2). Based on accelerated degradation testing, a hydrogel containing a 3 carbon linear alkyl group spacer is predicted to degrade over the course of 98 days. Upon formation of the macromonomer with a different alkyl group between the ester linkage and the terminal vinyl group of the macromonomer, a faster degradation rate can be engineered for the hydrogel, for instance a degradation rate of about 10% or higher, so as to provide a hydrogel that may degrade relatively quickly, over the course of a day, a few days, a few weeks, or several months.

While not wishing to be bound by any particular theory, it appears that variation of the chemistry of the di-functional monomer alters the chemical environment of the ester bonds of the macromonomer, including the susceptibility of the ester bonds to hydrolytic degradation. In particular, it appears that upon addition of a longer carbon chain between the ester linkage and the vinyl group, the degradation rate of the hydrogel can be decreased.

The hydrogels of the present invention may be shaped so as to be supplied in any suitable form for the desired application. For example, the hydrogel may be in the form of a thin film or slab, sphere, e.g., injectable microsphere or nanosphere, or an indeterminate, undefined shape that can be formed, for example, in situ after the precursor is injected into a void or defect site and polymerized.

The hydrogels of the present invention may be utilized as formed, for example, as a semi-permanent or temporary barrier or as an inter-layer. For instance, the degradable hydrogels may be utilized as tissue adhesives for wound closure and/or for the prevention of undesired adhesions, for instance in the prevention of post-surgical adhesions.

Optionally, the degradable hydrogels of the present invention may be loaded with an agent that may then be delivered from the hydrogel to a target device or tissue. For instance, the agent may be delivered from the hydrogel by diffusional release or as degradation of the encapsulating matrix proceeds or by a combination of both mechanisms. Hydrogel loading methods are generally known to those of skilled in the art and thus are not discussed at length herein. In general, however, polymeric carrier matrices such as those disclosed herein can be loaded with an agent during the formation of the hydrogel. Alternatively, an already formed hydrogel may be swollen in a solution of an agent so as to encapsulate the agent within the hydrogel.

The degradable hydrogels of the present invention may be suitable for biological applications including both in vivo and in vitro applications. For instance, the hydrogels may be utilized to carry, protect, and/or deliver one or more biologically active agents to a target cell or tissue. For example, the hydrogels can be utilized to deliver biologically active agents in the treatment, study, or prevention of disease or to encourage the healthy development of a biological system, including the development of individual cells in tissue engineering or gene therapy applications. The hydrogels may be particularly attractive for in vivo applications due to their biocompatibility both during use and following degradation of the networks. For example, the degradation products of a PEG-based hydrogel of the present invention may include the starting polymer (e.g., PEG) and biocompatible acids such as polyacrylic acid, glycolic acid, lactic acid, and the like; compounds that have been well characterized for their capability to be safely eliminated from a body via metabolic pathways.

The hydrogels of the present invention can be loaded so as to include a combination of materials if desired. For example, in one embodiment, the hydrogels may include live cells or agglomerations of live cells, for instance in tissue engineering applications. The biologically active materials to be delivered by the system may include growth and development factors for delivery to the living cells held within the hydrogel itself. In addition, the hydrogels may include cell membrane receptor ligands that can stimulate adhesion, spreading, and growth of cells. As such, the hydrogel, which can be considered a tissue engineering scaffold, may more closely resemble the extracellular matrix of a living organism, and thus can encourage the healthy development of the cells held in the hydrogel and can be formed so as to degrade at a rate roughly equivalent to the rate of growth and development of the encapsulated cellular construct.

Additional materials that may be included in a hydrogel of the present invention can include materials for targeting the hydrogel to particular cell or tissue types such as during in vivo utilization of the materials. For example, the hydrogel may include one member of a particular protein-ligand pair. In particular, the member may be present at the exterior surface of the formed hydrogel. Accordingly, the hydrogel can specifically associate with a cell or tissue that comprises the other member of the pair. Thus, the carrier matrix can be targeted to a particular type of cell or tissue or vice versa.

The hydrogels may be coated onto or otherwise applied to a carrier material. For example, the hydrogel may be coated on to or otherwise applied to a woven or non-woven web such as can be used as an externally applied dressing. The hydrogel may be coated on a surface of an implantable device. As the hydrogel degrades, a biologically active material loaded in the hydrogel can be released from the surface of the carrier material.

The present invention may be better understood by reference to the examples, below.

Example 1

Commercially available hydroxyl-terminated PEG having a number average molecular weight of 4000 was obtained from Aldrich Chemical Company of Milwaukee, Wis. PEG polymer was dissolved in dichloromethane with 1.8 times molar excess of triethylamine relative to PEG (not included for 3-chloropropionyl monomer) and cooled to zero degrees C. Twenty ml dichloromethane containing 4 fold molar excess of di-functional monomer relative to PEG was added dropwise with stirring. The reaction was maintained at zero degrees C. for 2 hours, then allowed to proceed for an additional 22 hours (46 hours for 3-chloropropionyl chloride) at room temperature with stirring. Monomers utilized included chloro acetyl chloride, 2-chloro propionyl chloride, 3-chloropropionyl chloride, and 4-chlorobutyryl chloride. Intermediates formed in these runs included PEG acetyl chloride, PEG 2-propionyl chloride, PEG-3-propionyl chloride, and PEG butyryl chloride. These intermediate products were purified by filtration of TEA:HCl salt, washing with sodium bicarbonate, then concentrated by rotary evaporation and repeatedly precipitated in ethyl ether. The final products were recovered by vacuum filtration and dried under vacuum. The formation of appropriate structures and overall reaction efficiencies greater than 90% were confirmed by proton nuclear magnetic resonance ($^1$H-NMR) using d-chloroform as solvent.

The intermediates were then separately reacted with 3 times molar excess relative to PEG of sodium acrylate or sodium methacrylate in DMF at varying temperatures for varying time points. PEG-bis-(2-chloro ethanoate) was reacted at 50 degrees C. for 24 hours, PEG-bis-(2-chloro propanoate) and PEG-bis-(3-chloro propanoate) for 24 hours at 70 degrees C., and PEG-bis-(4-chloro butanoate) for 24 hours at 100 degrees C. Residual sodium acrylate or methacrylate and sodium chloride by-product were removed by vacuum filtration, the products concentrated by rotary evaporation, precipitated in ethyl ether and recovered by filtration and dried under vacuum. Final acrylation efficiencies determined by $^1$H-NMR ranged from 95% for the PEG-bis-(2-chloro ethanoate) intermediate to 85% for the PEG-bis-(2-chloro propanoate) and PEG-bis-(3-chloro propanoate), and 90% for PEG-bis-(4-chloro butanoate).

The macromonomer preparation process was also carried out with each di-functional monomer for PEG starting materials having a number average molecular weight varying from 1000 to 8000 with equally successful results.

Example 2

Example 2 illustrates the synthetic route for PEG-bis-[2-acryloyl(oxy)ethanoate] in accordance with the method of the present invention.

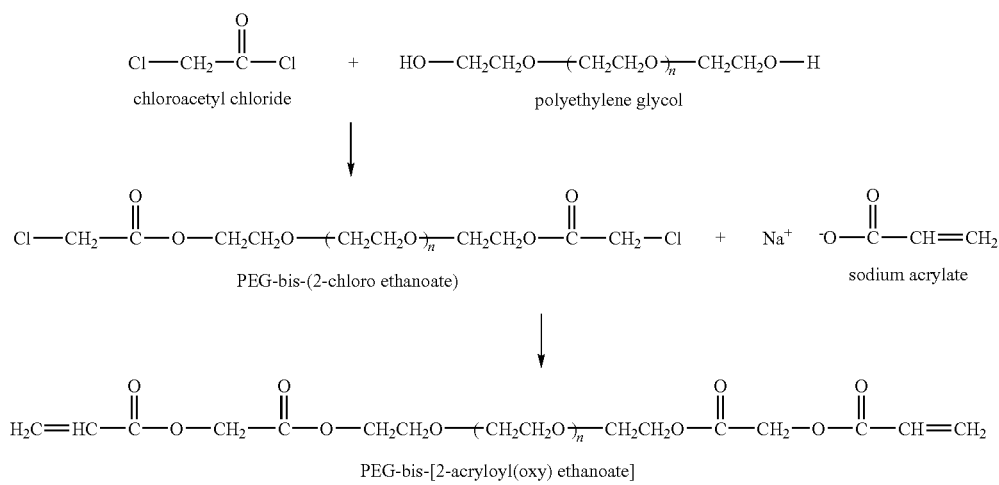

Example 3

Example 3 illustrates the synthetic route for PEG-bis-[2-acryloyl(oxy) propanoate] in accordance with the method of the present invention.

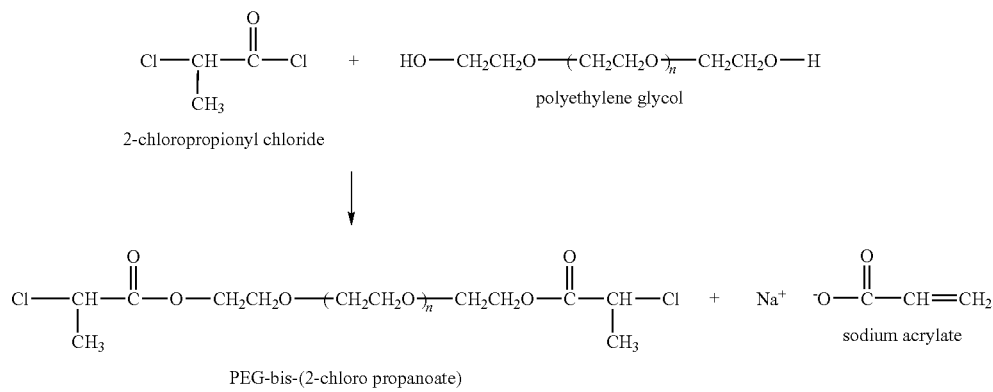

-continued
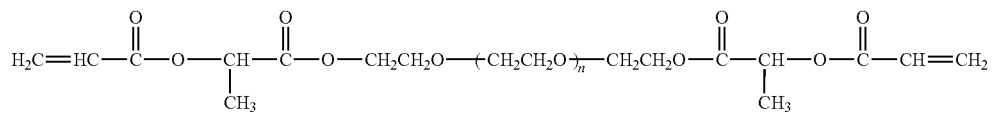
PEG-bis-[2-acryloyl(oxy) propanoate]
Example 4
Example 4 illustrates the synthetic route for PEG-bis-[3-acryl(oxy)propanoate] in accordance with the method of the present invention.
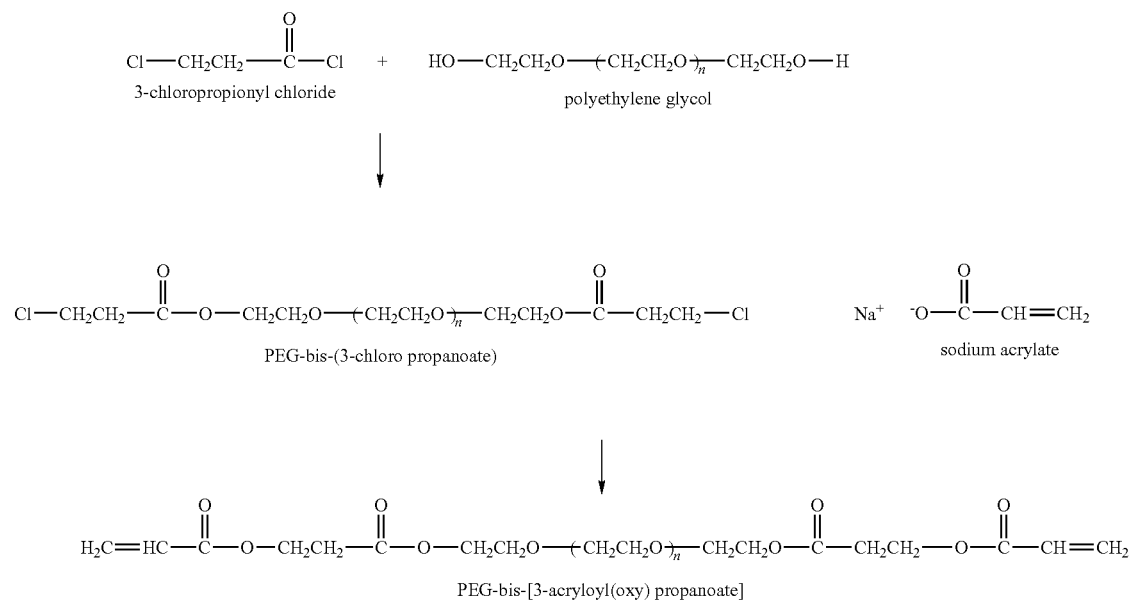
PEG-bis-[3-acryloyl(oxy) propanoate]
Example 5
Example 5 illustrates the synthetic route for PEG-bis-[4-acryloyl(oxy)butanoate] in accordance with the method of the present invention.
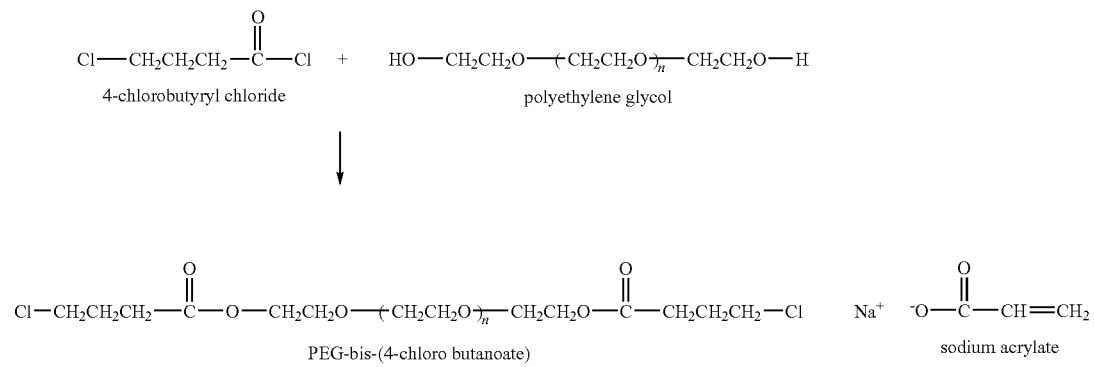

-continued

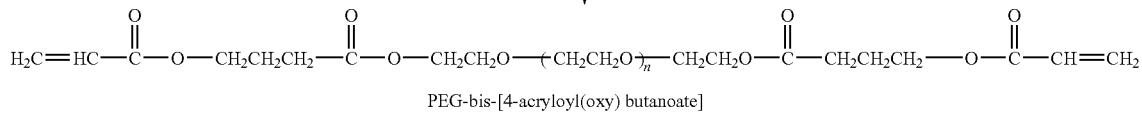

PEG-bis-[4-acryloyl(oxy) butanoate]

Example 6

To evaluate hydrogel degradation rates, aqueous solutions of the 4000 molecular weight macromonomer formed in Example 1 were prepared at 10% and 20% (w/v) with 0.24% (w/v) IGRACURE-651® photoinitiator. Solutions were injected between glass microscope slides separated by a 1 mm thick spacer and exposed to UV light (15 mW/cm$^2$) for 6-10 minutes. Samples were maintained in water for 24 hours to allow diffusive release of any unreacted macromonomer, and then dried by lyophilization and weighed (DWI). Samples were incubated in phosphate buffered saline (PBS) with 0.01% sodium at 37° C. with shaking. At various times, samples were retrieved, freeze-dried, and weighed (DWn).

Figure 3:
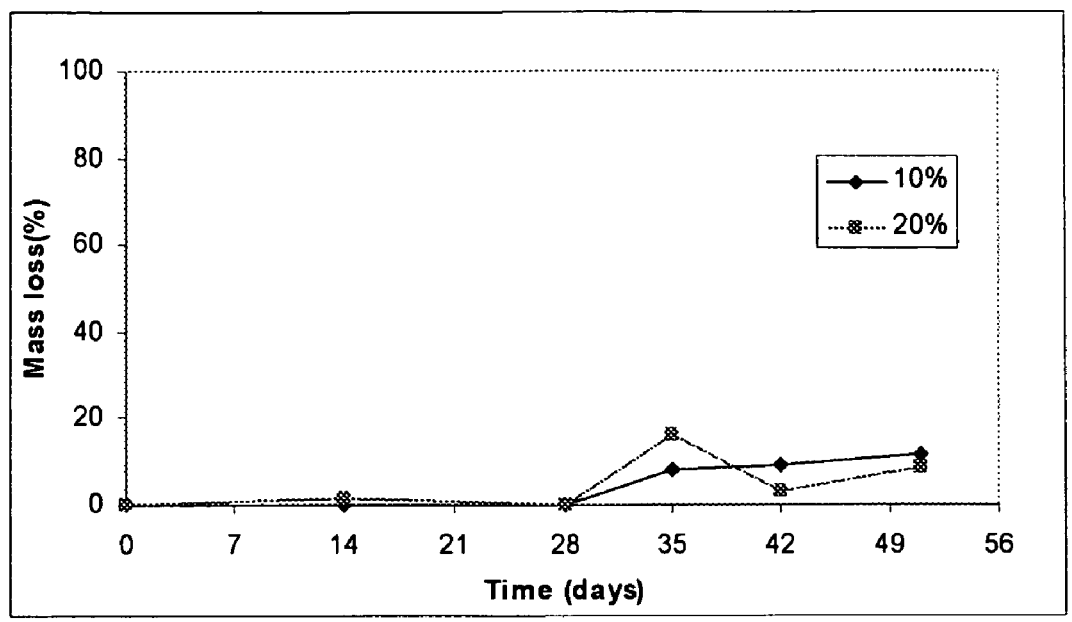
FIG. 3 illustrates the degradation rate of a hydrogel in accordance with the Examples of the present invention.

FIG. 1 illustrates the degradation rate, specifically mass loss (%) versus time (days) of the 10% and 20% (w/v) PEG-bis-[2-acryloyl(oxy)ethanoate] hydrogels (4000 MW). FIG. 2 illustrates the degradation rate of the 10% and 20% (w/v) PEG-bis-[2-acryloyl(oxy)propanoate (4000 MW). FIG. 3 illustrates the degradation rate of the 10% and 20% (w/v) PEG-bis-[4-acryloyl(oxy)butanoate] hydrogels (4000 MW). (Percent mass loss on the Figures is expressed as (DWI-DWn)/DWI×100%.)

Figure 4:
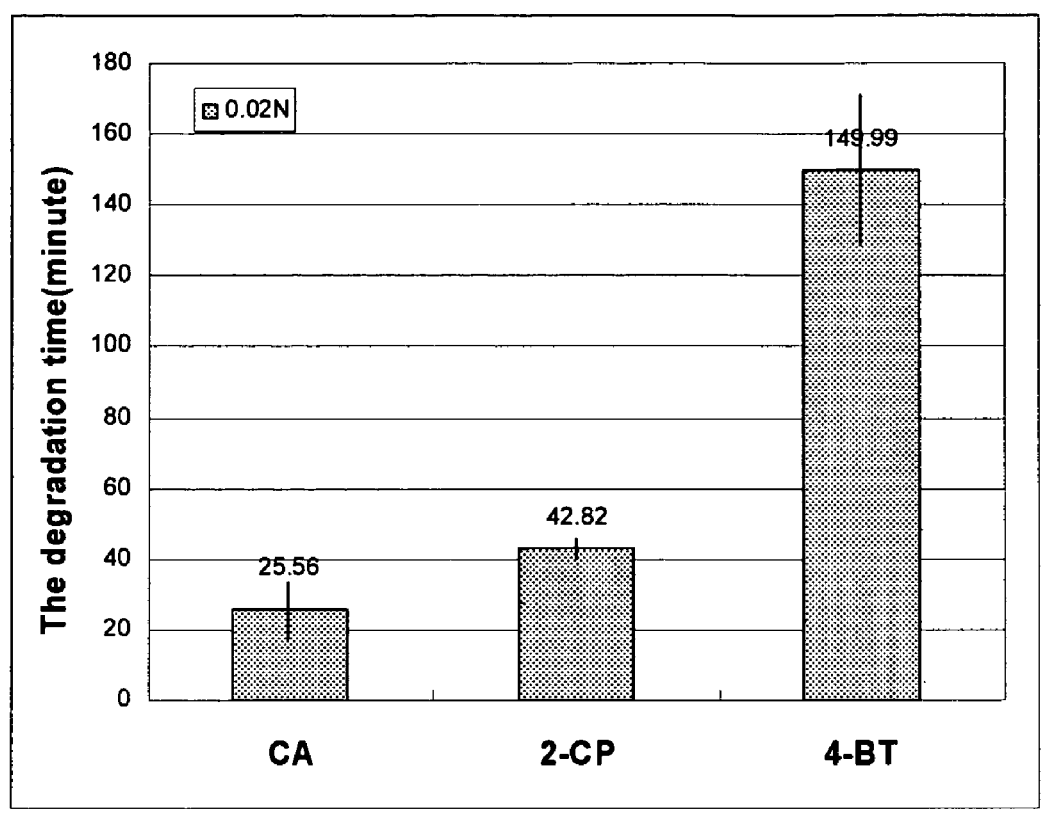
FIG. 4 illustrates the degradation rate of a hydrogel under accelerated degradation conditions in accordance with the Examples of the present invention.
Figure 5:
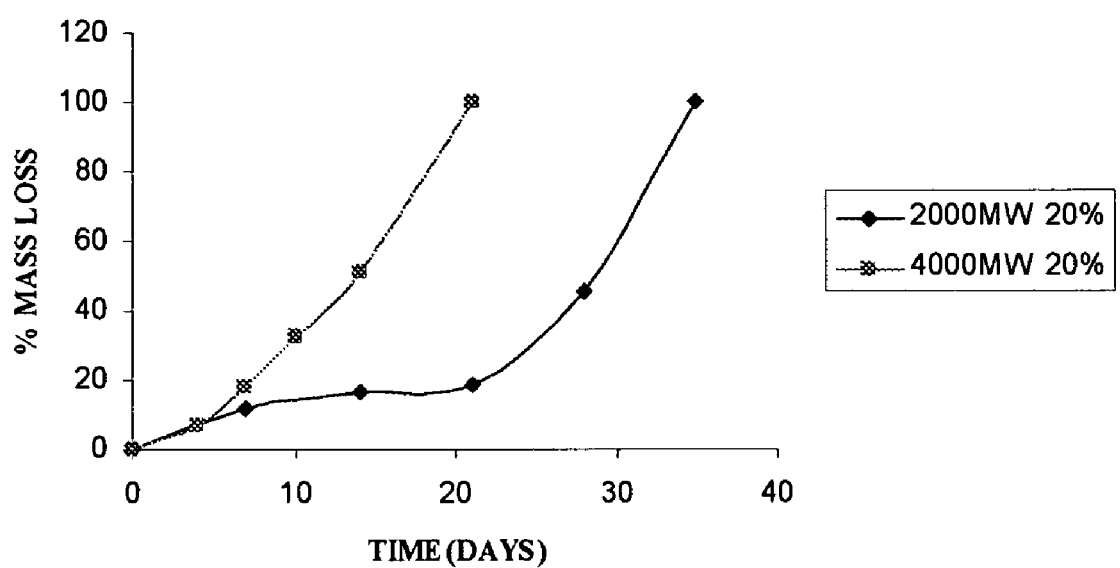
FIG. 5 illustrates degradation rate of a hydrogel in accordance with the Examples of the present invention.

As can be seen, variation of the degradation rate of the hydrogels can be attained through variation of the alkyl group included between the ester linkage and the terminal acrylate group. Due to the extended degradation time of the PEG PEG-bis-[4-acryloyl(oxy)butanoate], an accelerated degradation test was performed by carrying out the degradation incubation in 0.2 N sodium hydroxide. FIG. 4 graphically illustrates the accelerated degradation times of PEG-bis-[2-acryloyl(oxy)ethanoate] (CA), PEG-bis-[2-acryloyl(oxy)propanoate (2-CP) and PEG-bis-[4-acryloyl(oxy)butanoate] (4-BT). Degradation rates can also be influenced by the molecular weight of the starting hydrophilic polymer, with decreasing molecular weight resulting in prolonged degradation times. FIG. 5 illustrates the degradation rate of 20% (w/v) PEG-bis-[2-acryloyl(oxy)ethanoate] hydrogels polymerized from 2000 and 4000 MW polymers.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention that is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A macromonomer for preparation of a degradable hydrogel, the macromonomer formed by the process of reacting:
   a) a hydrophilic polymer including at least two hydroxyl groups with;
   b) a difunctional monomer to form an intermediate, the difunctional monomer comprising an acid halide group, an alkyl halide group, and a spacer that is a straight or branched alkyl group, wherein the acid halide group of the difunctional monomer reacts with one of the hydroxyl groups of the hydrophilic polymer such that the intermediate has a first ester bond on a backbone of the intermediate, the oxygen of the first ester bond being along the backbone of the intermediate and being between the hydrophilic polymer residue and the carbonyl group of the first ester bond, the intermediate including the alkyl halide group as a terminal group; and
   reacting the intermediate with
   c) a metallic salt of a vinyl acid monomer to form the macromonomer, wherein the terminal alkyl halide group of the intermediate reacts with the acid group of the vinyl acid monomer such that the macromonomer has a second ester bond on the backbone of the macromonomer, the oxygen of the second ester bond being along the backbone of the macromonomer and being between the alkyl group of the alkyl halide group and the carbonyl group of the second ester bond, the macromonomer having a terminal vinyl group;
   the macromonomer comprising the structure

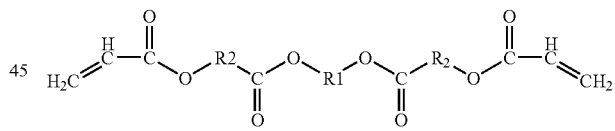

wherein R1 is the residue of the hydrophilic polymer, and
   R2 is the spacer that is a straight chain or branched alkyl group.

2. The macromonomer according to claim 1, wherein the macromonomer has a number average molecular weight between about 400 and about 100,000.

3. The macromonomer according to claim 1, wherein the hydrophilic polymer is selected from the group consisting of polyethylene glycol, polyvinyl alcohol, di- and tri-block copolymers of polyethylene glycol and polypropylene glycol, and a combination thereof.

4. The macromonomer according to claim 1, wherein R2 comprises 1 to 10 carbons.

5. The macromonomer according to claim 1, wherein R2 is a branched alkyl group.

6. The macromonomer according to claim 1, wherein R2 is a straight chain alkyl group.

7. The macromonomer according to claim 1, wherein the metallic salt of a vinyl acid monomer is sodium acrylate.

8. The macromonomer according to claim 1, wherein the metallic salt of a vinyl acid monomer is sodium methacrylate.

9. A macromonomer for preparation of a degradable hydrogel, the macromonomer formed by the process of reacting:
   a) a hydrophilic polymer including at least two hydroxyl groups, the hydrophilic polymer being selected from the group consisting of polyethylene glycol, di- and triblock copolymers of polyethylene glycol and polypropylene glycol, and a combination thereof with;
   b) a difunctional monomer to form an intermediate, the difunctional monomer comprising an acid halide group, an alkyl halide group, and a spacer that is a straight or branched alkyl group, wherein the acid halide group of the difunctional monomer reacts with one of the hydroxyl groups of the hydrophilic polymer such that the intermediate has a first ester bond on a backbone of the intermediate, the oxygen of the first ester bond being along the backbone of the intermediate and being between the hydrophilic polymer residue and the carbonyl group of the first ester bond, the intermediate including the alkyl halide group as a terminal group; and reacting the intermediate with
   c) a metallic salt of a vinyl acid monomer to form the macromonomer, wherein the terminal alkyl halide group of the intermediate reacts with the acid group of the vinyl acid monomer such that the macromonomer has a second ester bond on the backbone of the macromonomer, the oxygen of the second ester bond being along the backbone of the macromonomer and being between the alkyl group of the alkyl halide group and the carbonyl group of the second ester bond, the macromonomer having a terminal vinyl group;
the macromonomer comprising the structure

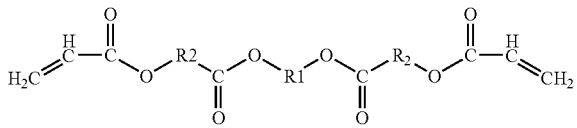

wherein R1 is the residue of the hydrophilic polymer, and
R2 is the spacer that is a straight chain or branched alkyl group.

10. The macromonomer according to claim 9, wherein the macromonomer has a number average molecular weight between about 400 and about 100,000.

11. The macromonomer according to claim 9, wherein R2 comprises 1 to 10 carbons.

12. The macromonomer according to claim 9, wherein R2 is a branched alkyl group.

13. The macromonomer according to claim 9, wherein R2 is a straight chain alkyl group.

14. The macromonomer according to claim 9, wherein the metallic salt of a vinyl acid monomer is sodium acrylate.

15. The macromonomer according to claim 9, wherein the metallic salt of a vinyl acid monomer is sodium methacrylate.

* * * * *